United States Patent [19]
Simonian et al.

[11] Patent Number: 5,905,150
[45] Date of Patent: May 18, 1999

[54] PROCESS FOR PREPARING ORGANOSILANES

[75] Inventors: Amy Kathleen Simonian, Ganseroort; Jimmy Lynn Webb, Ballston Lake; Daniel Joseph Brunelle, Burnt Hills; Timothy Edward Banach, Scotia; Slawomir Rubinsztajn, Niskayuna, all of N.Y.

[73] Assignee: General Electric Company, Schenecady, N.Y.

[21] Appl. No.: 08/917,968

[22] Filed: Aug. 27, 1997

[51] Int. Cl.$^6$ ............... C07D 251/00; C07F 7/04; C07F 7/08; C07F 7/10
[52] U.S. Cl. ............... 544/221; 556/414; 556/420; 556/440; 544/220
[58] Field of Search ............... 556/440, 414, 556/420; 544/220, 221

[56] References Cited

U.S. PATENT DOCUMENTS

| 3,517,001 | 6/1970 | Berger | 544/221 |
|---|---|---|---|
| 3,598,852 | 8/1971 | Berger | 556/414 |
| 3,607,901 | 9/1971 | Berger | 556/420 |
| 3,821,218 | 6/1974 | Berger | 544/220 |
| 4,946,977 | 8/1990 | Bernhardt et al. | 556/440 |
| 5,041,593 | 8/1991 | Plueddemann | 556/440 |
| 5,117,027 | 5/1992 | Bernhardt et al. | 556/440 |
| 5,132,423 | 7/1992 | Brunelle et al. | 544/162 |

*Primary Examiner*—Melvyn I. Marquis
*Assistant Examiner*—Mark W. Milstead
*Attorney, Agent, or Firm*—Noreen C. Johnson; Douglas E. Stoner

[57] ABSTRACT

An improved process for preparing a nitrogen or oxygen containing organoalkoxysilane such as an isocyanurate or fumarate by reacting a haloalkylaikoxysilane such as a chloropropytrimethoxysilane and a reactant of either a cyanate or an ammonium salt of an organic acid of C1–C20 carbon atoms or a metal salt of an organic acid of C1–C20 carbon atoms or mixtures thereof to a reaction temperature of at least about 80° C. to about 200° C., the improvement is in carrying out the reaction in the presence of a guanidinium salt phase as a transfer catalyst such as hexaethylguanidinium chloride. The improved process also is reacted wherein the temperature increase from the exotherm reaction above the reaction temperature ranges from about 0° C. to about 120° C. A preferred metal cyanate is sodium cyanate.

28 Claims, No Drawings

PROCESS FOR PREPARING ORGANOSILANES

FIELD OF THE INVENTION

This invention relates to a novel process of preparing certain organosilanes, particularly organoalkoxysilanes by reacting a certain silylorganohalide, particularly a haloalkylalkoxysilane, with certain chemical reactants in the presence of a guanidinium salt as a phase transfer catalyst at elevated temperatures.

BACKGROUND OF THE INVENTION

The use of tetraalkylammonium and hexaalkylguanidinium salts as phase transfer catalysts in the preparation of various polymers is known. In particular, U.S. Pat. No. 5,132,423 discloses the reaction of bisphenol salts with halo- or nitro-substituted phthalimides in an organic medium to produce bisimides which, upon conversion to dianhydrides and reaction with diamines, form polyetherimides. U.S. Pat. No. 5,229,482 discloses a similar phase transfer catalyst reaction of bisphenol salts with halo- or nitro-substituted bis(phthalimido) derivatives of aromatic diamines or with similar compounds, resulting in the direct formation of polyetherimides and other polyether polymers. The phase transfer catalysts employed according to U.S. Pat. No. 5,132,423 and 5,229,482 are guanidinium salts and especially hexaalkylguanidinium salts.

There are four general methods for the synthesis of an organoalkoxysilane compound:

1. Hydrosilylation of allyl- or vinyl-functional compound with trialkoxysilane.
2. Hydrosilylation of allyl- or vinyl-functional compound with trichlorosilane and subsequent alcoholysis.
3. Reaction of chioropropyltrimethoxysilane with a sodium or potassium salt of organic acid.
4. Reaction of an aminoalkysisane with a carbonate to form the product via the carbamate.

U.S. Pat. No. 3,517,001 discloses the first method and cites that isocyanurate-organosiianes have been prepared in the past by adding hydrosilanes to unsaturated isocyanates and more specifically allyl isocyanate in the presence of metal catalysts. This process is limited on a large scale because the hydrosilanes are expensive and the unsaturated isocyanates are typically highly toxic.

The first method suffers from many practical problems such as a slow hydrosilylation process, formation of byproducts containing internal olefins, use of toxic and low flash point reagents such as trimethoxy- or triethoxysilane.

The second method is described in U.S. Pat. No. 4,281,145. It teaches that bis(3-trimethylsilylpropyl) fumarate can be made by the hydrosilylation of diallyl maleate with trichlorosilane and subsequent methoxylation of the trichlorosilyl compound to the desired product. Unfortunately, the handling of trichlorosilane is very dangerous due to the low boiling point, very high reactivity and toxicity of this material. Also the methanolysis process is difficult to control and produces large amounts of waste.

The third method is described in U.S. Pat. Nos. 3,607,901; 3,821,218, and 3,598,852. These methods are for synthesizing 1, 3, 5-tris (trialkoxysilylpropyl) isocyanurates. This process involves the reaction of potassium cyanate with chloropropyltnmethoxysilane in a polar aprotic solvent such as N,N dimethylformamide (DMF) which is toxic and difficult to remove. The reaction time is about 3 to 8 hours. The resulting material has purity about 70% and is highly colored.

Patents such as U.S. Pat. No. 5,218,133 and U.S. Pat. No. 4,880,927 disclose the fourth method and disclose that aminoalkylsilanes can be reacted with carbonates such as dimethyl carbonate in basic conditions which will form the carbamate. The carbamate is then neutralized and converted to the isocyanurate by a lengthy, high temperature, subatmospheric pressure cracking reaction which necessitates the use of a cracking catalyst such as aluminum triethoxide and a base catalyst such as sodium acetate.

U.S. Pat. No. 4,946,977 discloses the preparation of methacryloxypropyltrimethoxysilane by contacting potassium methacrylate with chloropropyltrimethoxysilane in the presence of tetraalkylammonium halides as phase transfer catalyst. The yield of the reaction is below 90% and the resulting product usually has a dark color due the thermal decomposition of the catalyst.

European patent application 483,480 describes the preparation of methacryloxypropyltrimethoxysilane with high yield by the contacting of potassium methacrylate with chloropropyltrimethoxysilane in the presence of 4-N,N-dialkylaminopyridine as a catalyst. 4-Dialkyiaminopyridine is an effective catalyst in these processes but the use of dialkylaminopyridine is limited due to very high toxicity of these compounds.

SUMMARY OF THE INVENTION

This invention relates to a novel process for preparing organoalkoxysilanes by employing a guanidinium salt as a phase transfer catalyst for forming organoalkoxysilanes having reduced color. The guanidinium salts are less toxic than prior art catalysts, and have improved thermal stability. Basically, the process comprises reaction of a haloalkyialkoxysilane with a chemical reactant which may be either a cyanate, an ammonium salt of an organic acid having 2–20 carbon atoms or an alkali metal salt of an organic acid having 2–20 carbon atoms. The reaction is carried out in the presence of a guanidinium salt as a phase transfer catalyst and at elevated temperatures.

In addition, the invention relates to an improved process for producing organoalkoxysilanes wherein the reaction exotherm i.e. the evolution of heat is controlled thereby enhancing the commercialization of the process for producing organoalkoxysilanes at a substantial reduced risk as described hereinafter.

DETAILED DESCRIPTION OF THE INVENTION

In the practice of the process of this invention, a critical feature of the process is the utilization of a guanidinium salt as a phase transfer catalyst to prepare the organoalkoxysilanes. The guanidinium salts that may be employed herein have the following formula:

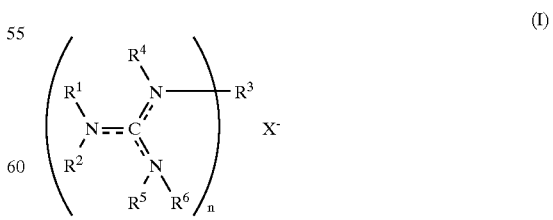

(I)

wherein $R^{1-2}$ and $R^{4-6}$ are independently selected from the group consisting of alkyl of 1–12 carbons preferably 2–6 carbons, cycloalkyl, phenyl; $R^3$ is alkyl or alkylene of 1–12 and preferably 2–6 carbons, or each $R^{1-2}$, $R^{3-4}$ and $R^{5-6}$ pair together with N attached thereto is piperidino or pyrrolidino or morpholino; X⁻ is a halogen, boron fluoride (BF4), alkyl sulfonate, hydrogen sulfate, sulfates or carboxylates; and n is 1 or 2. Preferably, the guanidinium salt is a phase transfer catalyst having an hexaallkylguanidinium moiety wherein the alkyl is an aliphatic hydrocarbon radical having up to 40 carbons atoms such as hexaethylguanidinium, hexabutylguanidinium, and tetraethyldibutylguanidinium, and the like, and mixtures thereof. More particularly the guanidinium salt catalyst of this invention may be any of the guanidinium salts of the above formula containing about 12–30 carbon atoms. The guanidinium catalysts such as hexaethylguanidinium halide are significantly less toxic than other catalyst such as 4-(N,N-dimethylamino)pyridine and further have better thermal stability.

Another reactant employed in the practice of this invention to prepare the organoalkoxysilanes is a silane, particularly, a haloalkylaikoxysilane. Those haloalkylalkoxysilanes which can be utilized in this invention are, for example but not limited thereto, chloropropytrimethoxysilane, bromopropyltrimethoxysilane, chlorobutyldimethylethoxysilane, chloropropyltriethoxysilane, chloropropylmethyldimethoxysilane, chlorobutylphenylmethyl-n-propoxysilane, iodopropyltrimethoxysilane, and the like, and mixtures thereof.

In the first embodiment of the process of this invention, another reactant is selected from the group consisting essentially of a cyanate, an ammonium salt of an organic acid and an alkali salt of an organic acid which is reacted with the haloalkylalkoxysilane to produce a silylalkoxyorgano isocyanurate. The cyanates which may be employed in the practice of this invention are metal cyanates, for example, but not limited thereto, lithium, sodium, potassium, rubidium, barium, strontium, silver, lead, mercury, calcium cyanates, and the like, and ammonium cyanate and phosphonium cyanate. The preferred cyanate is sodium cyanate.

The silylalkoxyorgano isocyanurates produced by this embodiment may be of the following formula:

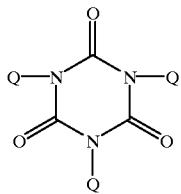

(II)

where Q is $(RO)_{3-a}R'SiR''—$ and a is 1–3. Some of the isocyanurates which are included by Formula 2 are, for example, 1,3,5-tris(trimethoxysilylpropyl) isocyan urate,
1,3,5-tris(methyldimethoxysilylpropyl) isocyanurate,
1,3,5-tris(dimethylethoxysilylbutyl) isocyanurate,
1,3,5-tris(phenylmethylmethoxysilylpropyl) isocyanurate, and the like.

In a second embodiment for producing organoalkoxysilanes of this invention, the organoalkoxysilane is prepared by reacting at elevated temperatures the haloalkylaikoxysilane and an ammonium salt of an organic acid having 2–20 carbon atoms or an alkali metal salt of an organic acid having 2–20 carbon atoms. It has been found that organoalkoxysilanes can be prepared with a high yield by the novel process of this invention. By this process, the use of a toxic solvent or any solvent to facilitate the reaction is not required.

The ammonium salt of an organic acid having 2–20 carbon atoms may be any such ammonium salt thereof. Preferably the organic acids suitable herein are maleic, fumaric, succinic, adipic and the like. The preferred organic acid is fumaric. The alkali metal salt of an organic acid having 2–20 carbon atoms may be the alkali metal salt of any such organic acid. The organic acids that my be employed are preferably maleic, fumaric, succinic, adipic and the like. The metal salts are preferably selected from, but not limited thereto, lithium, sodium, potassium, rubidium, barium, strontium, silver, lead, mercury, calcium, and the like. The preferred alkali metal is sodium or potassium.

The following organoalkoxysilanes can be prepared by this second embodiment:

 (III)

 (IV)

 (V)

where x is 1,2 or 3; y is 1–12; Z is an alkoxy group of 1–12 carbon atoms, or cycloalkoxy of 5–9 carbon atoms or an aryloxy; $R^1$ is an alkyl group of 1–12 carbon atoms or cycloalkoxy or phenyl. A is either —O(O)C—,
—NH(O)C—,
—NR¹(O))C—,
=N(O)C—,
—O(O)P=, or
—O(O)CO— wherein $R^2$ is an alkyl group of 1–12 carbon atoms, cyclohexyl, phenyl, —CH=CH₂, —C(CH₃)=CH₂, or —CH=CH—.

In a third embodiment of this invention, a novel process is employed to produce organoalkoxysilanes by reacting either a cyanate, an ammonium salt of an organic acid or an alkali metal salt of an organic acid with a haloalkylalkoxysilane in the presence of a guanidinium catalyst at elevated temperatures and either at a controlled rate of reaction or controlled reaction conditions such as reaction temperature and catalyst amount. The process disclosed in this embodiment controls the evolution of heat over an optimized amount of time and thus provides a safer yet efficient reaction. Employing this process results in a significant decrease in the change in temperature above the reaction temperature due to the evolution of heat. This process as hereinafter described in more detail discloses the processing conditions for preparing isocyanurates such as 1,3,5-tris [(trialkoxysilyl)alkyl] isocyanurates and other organoalkoxysilanes. These organoalkoxysilanes are prepared by simply combining a haloalkylalkoxysilane with the reactants set forth above and a guanidinium catalyst and heating to an elevated temperature and by controlling the rate of the reaction by a solids or a slurry addition to form the neat liquid isocyanurate product. The process does not utilize solvents and can be a one vessel reaction without requiring the isolation of hazardous isocyanates, is faster than prior art reactions and can be run at lower temperatures in the absence of specific pressures as disclosed in the prior art. The main benefit of the process of this embodiment is that the increase in temperature from the evolution of heat from the reaction is minimal, allowing the process to be carried out on a commercial scale with reduced risk.

In the slurry addition method for controlling the rate of reaction, the process comprises forming a slurry of at least a portion of the reactants without catalyst, separately heating the balance of reactants with catalyst to a temperature of at least about 80° C., adding the slurry at such a rate to the heated balance of reactants and catalyst as to maintain the temperature between about 80° C. and about 200° C., preferably from 100° C. to about 180° C., agitating the mixture for a period of time sufficient to form the organoalkoxysilanes and recovering the organoalkoxysilane. A temperature profile of the reaction temperature shows a temperature increase from the evolution of heat from the reaction ranging from about 0° C. to about 50° C., preferably 020 C. about 30° C. and typically from about 10° C. to about 2020 C. above the reaction temperature. It should be understood that in the practice of the process described, metering of at least a portion of the reactants controls the rate of the reaction thereby minimizing the chance of a run away reaction from the fast emergence of heat from the reaction.

In a solids addition, the rate of reaction is controlled by a process of first heating a mixture of a haloalkylalkoxysilane and guanidinium catalyst to a temperature of at least about 80° C. The other reactant in solid form is added at a controlled rate to the heated mixture. The rise in temperature above the reaction temperature from the evolution of the heat of reaction is minimized again as disclosed in the slurry addition process above.

As shown by the examples, the evolution of heat can also be controlled even by the addition of at least a stoichiometric amount of the reactants and then heating the reactants to the reaction temperature as set forth previously. However, in this embodiment of this invention, the rise of temperature above the temperature of reaction from the evolution of heat can be achieved by controlling the quantity of catalyst employed and the temperature to which the reactants are heated. For example with a greater amount of guanidinium catalyst, a lower temperature can be employed to which the reactants are heated to initiate the reaction. On the other, with a controlled higher temperature of reaction and a lower amount of guanidinium catalyst, the reactants can be heated to a higher temperature to initiate reaction with little or no evolution of heat from the reaction.

The amount of guanidinium catalyst that may be employed herein ranges from about 0.001 mole % to about 4 mole % and preferably about 0.001 mole % to about 2.0 mole %. The temperature to which the reactants can be heated is as set forth previously and can range from about 80° C. to about 200° C. The control of temperature and catalyst can be varied within the limits set forth above in order to control or minimize the rate of evolution of heat from the reaction. By controlling the rate of evolution of heat from the reaction, which is not the temperature to which the reactants are heated to initiate reaction, little or no discernible temperature rise is achieved.

In general, the process herein disclosed comprises reacting (1) a haloalkylalkoxysilane (2) a chemical reactant selected from the group consisting essentially of a cyanate salt, an ammonium salt of an organic acid having 2–20 carbon atoms, an alkali metal salt of an organic acid of 2–20 carbon atoms, and mixtures thereof, (3) a guanidinium salt as a phase transfer catalyst, (4) at elevated temperatures for a period of time to produce an organoalkoxysilane, and (5) recovering the organoalkoxysilane. The organoalkoxysilanes can be nitrogen or oxygen containing organoalkoxysilanes such as the isocyanurates and fumarates. The elevated temperatures to which the reactants may be heated ranges about 80° C. to about 200° C. and preferably about 100° C. to about 180° C. and more particularly about 125° C. to about 160° C. Since the reaction evolves heat, the temperature of the reaction may exceed 180° C. and can reach 200° C. or higher without additional heat being supplied. The process time can vary from several minutes to over an hour or more depending on the process conditions employed as described above and as demonstrated in the examples to follow.

As disclosed herein in one embodiment, the conditions of the process can be selected to produce an organoalkoxysilane such as an isocyanurate or fumarate at a lesser temperature increase due to the controlled evolution of heat from the reaction without utilizing solvents. The increase in temperature from the reaction above the temperature to which the reactants are heated to commence reaction can be about 0° C. to about 120° C. It is preferred to control the rate of reaction to minimize the temperature increase from the exothernic reaction from about 0° C. to about 50° C.

This invention is further disclosed by means of the following examples. It is understood, however, that this invention shall in no way be restricted by these examples. In the examples where amounts are in terms of percent, they are percent by weight unless otherwise stated.

EXAMPLE 1

In a 100 mL three neck flask equipped with a mechanical stirrer, condenser and nitrogen inlet, 0.1 mole (19.87 g) of chloropropyltrimethoxysilane was combined with 0.1 mole (7.15 g) 90% sodium cyanate and 0.005 moles (1.14 g) of hexaethylguanidinium bromide under nitrogen. The temperature was raised to 130° C. for 1 hour and 10 minutes. The mixture was then cooled to room temperature and vacuum filtered through filter aid. The filter cake was washed with methylene chloride. The methylene chloride was then stripped off. The final product was a clear, light yellow compound, and a yield of 81.7% was obtained. Proton nuclear magnetic resonance ($H^1$NMR) revealed 75% purity. Gas chromatography (GC) and mass spectophotometry (MS) confirmed the molecule with molecular weight of 615, as calculated for the structure below.

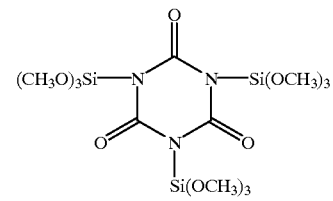

EXAMPLE 2

Synthesis of Bis(3-Trimethoxsilylpropyl) Fumarate in the Presence of Hexaethylguanldinum Bromide The reaction mixture was protected from moisture by a nitrogen blanker. 249 g. (1.25 mol) of 3-chloropropyltrimethoxysilane was placed in 1000 ml round bottomed flask equipped with a thermometer, condenser, addition funnel and mechanical stirrer. Subsequently 100 g (0.625 mol) of disodium fumarate and 3.36 g of hexaethylguanidinum bromide were added while maintaining stirring. After the addition was completed, the reaction mixture was heated to 135° C.±5° C. over a period of 8 hours. When GC analysis showed the conversion of 3-chloropropyltrimethoxysilane of greater than 90%, the reaction was cooled to 50° C. At this temperature 260 g of Isopar C (a petroleum ether boiling in the range of 50–110°

C.) was added. After 10 minutes of stirring the precipitate (mostly NaCl) was filtered off using a Buchner funnel. The light-yellow liquid was placed back into the flask and solvent was removed by vacuum distillation at 60° C. and 50 mm Hg with the excess of 3-chloropropyltrimethoxysilane being stripped off at 120° C. and 20 mmHg with a nitrogen sparge. The resulting low viscosity (below 20 cSt) light yellow fluid was filtered to give 235 g (85% yield) of the final product. The structure of this material was confirmed by proton, $Si^{29}$ NMR and GC-MS and is as follows:

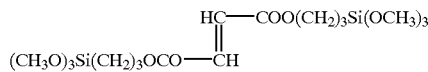

EXAMPLE 3
Synthesis of Bis(3-Trimethoxysilylpropyl) Fumarate in the Presence of Prior Art Catalyst Tetrabutylammonium Bromide The reaction mixture was protected from moisture by a nitrogen blanket. 249 g. (1.25 mol) of 3-chloropropyltrimethoxysilane was placed in a 1000 ml round bottomed flask equipped with thermometer, condenser, addition funnel and mechanical stirrer. Subsequently 100 g (0.0625 mol) of disodium fumarate and 2.5 g of tetrabutylammonium bromide were added while maintaining stirring. After the addition was completed, the reaction mixture was heated to 140° C.±5° C. At this temperature 260 g of Isopar C was added. After 10 minutes of stirring the precipitate was filtered off with the use of a funnel. The dark-brown liquid was analyzed by GC. The yield of the bis(3-trimethoxysilylpropyl) fumarate was estimated at about 10%.

EXAMPLE 4
Synthesis of Bis(3-Trimethoxysilylpropyl) Fumarate the Presence of Prior Art Catalyst Dimethylaminopyridine The reaction mixture was protected from moisture by a nitrogen blanket. 249 g. (1.25 mol) of 3-chloropropyltrimethoxysilane was placed in 1000 ml round bottomed flask equipped with thermometer, condenser, addition funnel and mechanical stirrer. Subsequently 100 g (0.625 mol) of disodium fumarate and 2.44 g of dimethylaminopyridine were added while maintaining stirring. After the addition was completed, the reaction mixture was heated to 140° C.±5° C. over a period of 14 hours. When GC analysis showed the conversion of 3-chloropropyltrimethoxysilane was greater than 80%, the reaction was cooled to 50° C. At this temperature 260 g of Isopar C was added. After 10 minutes of stirring the precipitate (mostly NaCl) was filtered off with the use of a funnel. The light-yellow liquid was placed back into the flask and solvent was removed by vacuum distillation at 60° C. and 50 mm Hg with the excess of 3-chloropropyltrimethoxysilane being stripped off at 120° C. and 20 mm Hg with a nitrogen sparge. The resulting low viscosity (below 20 cSt) light yellow fluid was filtered to give 220 g (80% yield) of the final product. The structure of this material was confirmed by proton, Si29 NMR and GC-MS.

EXAMPLE 5
The following examples demonstrate the third embodiment of the invention having a low exotherm, i.e. low temperature increase in forming isocyanurates.

A. Slurry Addition. In a 500 mL three neck flask equipped with a mechanical stirrer 244.8 g of chloropropyltrimethoxysilane and 171.6 g of sodium cyanate were charged. The mixture was stirred to create a consistent slurry. A 1000 ml three neck flask equipped with a mechanical stirrer, and a thermometer in line with a Thermowatch® unit was charged with 193.4 g of chloropropyltrimethoxysilane and 2.6 g of hexaethylguanidinium chloride. This vessel was then heated to 145° C. A peristaltic pump connected the two vessels using tubing with glass rods fed through the thermometer's adapter and was inserted into each vessel. When the vessel containing the catalyst was at temperature, the slurry was fed into this mix from the second vessel at a rate of 4.3 ml per minute for 1 hour. The temperature profile of this reaction is listed in Table 1 below.

TABLE 1

REACTION TEMPERATURE AS A FUNCTION OF TIME

| Time (min) | Temperature (°C.) |
| --- | --- |
| 0 | 145 |
| 7 | 147 |
| 10 | 150 |
| 15 | 153 |
| 20 | 155 |
| 25 | 158 |
| 30 | 160 |
| 36 | 161 |
| 40 | 162 |
| 45 | 161 |
| 50 | 160 |
| 55 | 158 |
| 60 | 155 |
| 90 | 145 |

After the addition was complete (60 minutes), the mixture was stirred for 3 additional hours after which the mixture was cooled to room temperature. A filter aid (5.45 g) was added and the mixture was stirred for 30 minutes and then pressure filtered. A yellow liquid product was yielded. Proton NMR revealed 90+ mol % purity. NMR-GC-MS confirmed the molecule with a molecular weight of 615, as calculated for the isocyanurate.

B. Solids Addition. In a 50 ml three neck flask equipped with thermometer and temperature controller, a mechanical stirrer and a solids screw feeder addition funnel with a nitrogen inlet, 19.87 g of chloropropyltrimethoxysilane and 0.26 g of hexaethylguanidinium chloride catalyst were charged and heated to 145° C. 7.15 g of sodium cyanate was charged into the solids screw feeder addition funnel. When the temperature reached 145° C., the solids were added via the funnel at a approximately 0.24 g/min over 30 minutes. A slightly lesser temperature increase than in Part A above was observed. The maximum temperature reached was about 160° C. After the addition was complete the reaction temperature reached to about 145° C. and was stirred at this temperature for about 2 hours. After 2 hours the reaction was cooled to room temperature and 1 wt. % of filter aid was added. Petroleum ether was added to the mix to remove some catalyst and the mixture was then filtered and stripped of solvent. Conversion of 93 mol % was achieved. The product was a yellow color. The structure was confirmed by NMS and GC.

As demonstrated by the above Examples Part A and B, the temperature increase from the exothermic reaction was only about 17° C. (Part A) and about 150° C. (Part B).

EXAMPLE 6
On a 50 ml flask equipped with a mechanical stirrer, thermometer, temperature controller, condenser and nitrogen inlet 19.87 g (0.10 mole) of chloropropyltrimethoxysilane, 7.37 g (0.11 mole) of sodium cyanate and 0.53 (2 mole %) of hexaethylguanidinium chloride were charged. The temperature was brought to 100° C. and held for 1 hour. During this time a 31° C. exotherm was observed. The reaction was cooled and 40 ml of petroleum ether (b. p. 50–10° C.) and 0.5 g of Celite filter aid were added and the mixture was allowed to stir for 30 minutes. The mixture was then filtered to yield 94.4 mole % of the light yellow product. The structure was confirmed by both proton NMR and GC-MS.

EXAMPLE 7

In a 50 ml flask equipped with a mechanical stirrer, thermometer, temperature controller, condenser and nitrogen inlet 19.87 g (0.10 mole) of chloropropyltrimethoxysilane, 7.37 g (0.11 mole) of sodium cyanate and 0.13 g (0.25 mole %) of hexaethylguanidinium chloride were charged. The temperature was brought to 160° C. and held for 1 hour. During this time, less than 3° C. exotherm was observed. The reaction was cooled and 40 ml of petroleum ether (b. p. 30–110° C.) and 0.5 g of filter aid were added and the mixture was allowed to stir for 30 minutes. The mixture was then filtered to yield 70.4 mole % of the yellow product. The structure was confirmed by both proton NMR and GC-MS.

EXAMPLE 8

Example 1 was essentially repeated except for the quantities of reactants including catalyst employed herein. The temperature to which the reactants were heated was the same temperature used in Example 5, Part A and Part B, namely 145° C.

In a 100 ml 3 neck flask equipped with a reflux condenser, nitrogen inlet, mechanical stirrer, thermometer and temperature controller, 39.74 g of chloropropyltrimethoxysilane, 14.3 g sodium cyanate and 0.13 g (0.25 mol %) of hexaethylguanidinium chloride were combined. The temperature was raised to 145° C. at the same rate as in Example 5. The temperature profile as the reaction commenced was as set forth in Table 2 below.

TABLE 2

TEMPERATURE AS A FUNCTION OF TIME

| Time (min) | Temperature (°C.) |
|---|---|
| 0 | 145 |
| 5 | 160 |
| 9 | 190 |
| 10 | 200+ |

As demonstrated by this Example 6, even though it is a process embodiment of this invention, the exotherm of the reaction raised the temperature in excess of 55° C. compared to the temperature increase of 17° C. and 15° C. in Part A and Part B of Example 5.

The reaction products of the process of this invention are useful as fiber treatment and automotive coatings. The nitrogen-containing organosilanes and copolymers are also known for imparting water repellence in various substrates such as fibers. Other organosilanes prepared herein are useful as coupling agents and adhesion promoters.

Although the invention has been described by reference to particular illustrative embodiments thereof, many variations and modifications of this invention may become apparent to those skilled in the art without departing from the spirit and scope of this invention as set forth in the appended claims hereto.

What is claimed is:

1. A process for preparing an organoalkoxysilane which process comprises reacting at an elevated temperature (1) a haloalkylalkoxysilane, (2) a reactant selected from the group consisting essentially of a cyanate, an ammonium salt of an organic acid of $C_2$–$C_{20}$ carbon atoms, an alkali metal salt of an organic acid of $C_2$–$C_{20}$ carbon atoms, and mixtures thereof, and (3) a phase transfer catalyst comprising a guanidinium salt.

2. The process of claim 1 wherein the guanidinium salt catalyst is a hexaalkylguanidinium salt.

3. The process of claim 2 wherein the alkyl group of the hexaalkylguanidinium salt is an aliphatic hydrocarbon of $C_1$–$C_{20}$ carbon atoms.

4. The process of claim 1 wherein the organoalkoxysilane is a nitrogen-containing organoalkoxysilane.

5. The process of claim 4 wherein the nitrogen-containing organoalkoxysilane is an isocyanurate.

6. The process of claim 5 wherein the isocyanurate is 1,3,5-tris[(trialkoxysiyl)alkyl]isocyanurate.

7. The process of claim 1 wherein the organoalkoxysilane is an oxygen containing organoalkoxysilane.

8. The process of claim 1 wherein the cyanate is selected from the group consisting of metal cyanate, an ammonium cyanate and a phosphonium cyanate.

9. The process of claim 8 wherein the cyanate is a metal cyanate.

10. The process of claim 9 wherein the metal cyanate is sodium cyanate.

11. The process of claim 7 wherein the oxygen containing organoalkoxysilane is a carboxylate.

12. The process of claim 11 wherein the carboxylate is a fumarate.

13. The process of claim 12 wherein the fumarate is bis(3-trimethoxysilylpropyl) fumarate.

14. The process of claim 1 wherein the haloalkylalkoxysilane has an alkyl hydrocarbon group of C 1–C20 carbon atoms.

15. The process of claim 14 wherein the haloalkylalkoxysilane is a chloroalkylalkoxysilane.

16. The process of claim 15 wherein the haloalkyoalkoxysilane is chloropropyltrimethoxysilane.

17. The process of claim 1 wherein the metal cyanate is sodium cyanate.

18. The process of claim 1 wherein the alkali metal salt of an organic acid is an alkali metal salt of a carboxylic acid.

19. The process of claim 18 wherein the alkali metal salt of a carboxylic acid is sodium fumarate.

20. The process of claim 1 wherein the reaction temperature to which the reactants are heated ranges from about 80° C. to about 200° C.

21. The process of claim 1 wherein the temperature from the evolution of heat from the reaction above that elevated temperature to which the reactants are heated is from about 0° C. to about 120° C.

22. The process of claim 21 wherein the temperature increase is from about 0° C. to about 50° C.

23. A process for preparing a nitrogen-containing organoalkoxysilane comprising the steps of (1) preparing a slurry of a reactive amount of a cyanate salt and at least a portion of the reactive amount of a haloalkyalkoxysilane, (2) separately preparing a mixture 5 of the balance of the reactive amount of a haloalkylalkoxysilane and a guanidinium salt as a phase transfer catalyst, (3) heating mixture (2) to a reaction temperature of at least about 80° C., (4) adding the slurry of (1) to mixture (2) at a controlled rate over a period of not less than 20 minutes, (5) continuing the reaction for a period of time sufficient to form the nitrogen-containing organoalkoxysilane, (6) during said reaction period, the temperature increase from the reaction does not exceed about 50° C., (7) cooling the reaction mixture, and (8) recovering the nitrogen-containing organoalkoxysilane.

24. The process of claim 23 wherein mixture (2) is heated to a temperature of at least about 100° C.

25. The process of claim 23 wherein the nitrogen-containing organoalkoxysilane is an isocyanurate.

26. The process of claim 23 wherein the isocyanurate is 1,3,5-tris[(trialkoxysilyl)alkyl]isocyanurate.

27. A process for preparing a nitrogen-containing organoalkoxysilane comprising the steps of (1) heating a mixture of a reactive amount of a haloalkylalkoxysilane and a guanidinium salt as a phase transfer catalyst to a reaction temperature of at least 80° C., (2) adding a metal cyanate to the heated mixture of (1) at a controlled rate, (3) continuing the reaction for a period of time sufficient to form the nitrogen-containing organosilane, (4) cooling the resulting reaction product, and (5) recovering the reaction product.

28. The process of claim 27 wherein the nitrogen-containing organoakoxysilane is an isocyanurate.

* * * * *